United States Patent [19]

Lee et al.

[11] 4,416,829

[45] Nov. 22, 1983

[54] POLY-HINDERED PHENOL-PHOSPHITES AND PROCESS FOR PREPARATION

[75] Inventors: Richard J. Lee, Downers Grove; Adam S. Kurasiewicz, Wheaton, both of Ill.; Eugene E. Richardson, Kerrville, Tex.

[73] Assignee: Standard Oil Company (Indiana), Chicago, Ill.

[21] Appl. No.: 433,009

[22] Filed: Oct. 6, 1982

[51] Int. Cl.³ .............................................. C07F 9/15
[52] U.S. Cl. ............................... 260/927 R; 260/936; 260/982; 252/48.4
[58] Field of Search .................... 260/982, 936, 927 R

[56] References Cited

U.S. PATENT DOCUMENTS 3,876,709  4/1975  Lee et al. ............................ 568/718
4,196,117  4/1980  Spivack .............................. 260/936

Primary Examiner—Anton H. Sutto
Attorney, Agent, or Firm—Richard A. Kretchmer; William T. McClain; William H. Magidson

[57] ABSTRACT

Cyclic phosphite structure-containing polyalkyl hindered phenol tetramers are disclosed as novel compounds useful to impart to lubricant oils oxidation and corrosion inhibition. A novel preparative method for the cyclic phosphite-containing polyalkyl hindered phenol tetramers is also disclosed wherein at least a molar excess of a tri($C_1$ to $C_4$ alkyl) phosphite is reacted in the presence of iodine as catalyst with a polyalkyl hindered phenol tetramer of the formula:

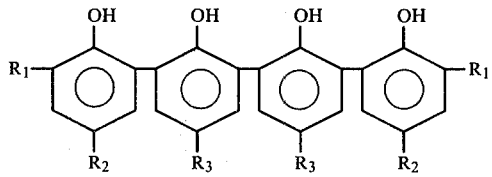

wherein the sum of the carbon atoms in all the $R_1$, $R_2$, and $R_3$ groups is at least 42 and wherein $R_1$ and $R_2$ can be $C_1$ to $C_{12}$ alkylhydrocarbon groups and the $R_3$ groups can each have as many as 200 carbon atoms. The trialkyl phosphite reacts with a pair of adjacent hydroxyl groups to split out 2 molecules of alkanol and form the cyclic phosphite structure:

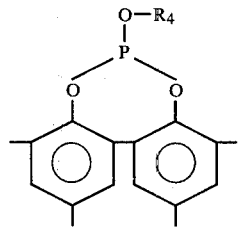

within said tetramer structure. Said $R_4$ group is the $C_1$ to $C_4$ alkyl from the trialkyl phosphite.

11 Claims, No Drawings

POLY-HINDERED PHENOL-PHOSPHITES AND PROCESS FOR PREPARATION

This invention relates to a poly-hindered alkylphenol mono- and disphosphite as a novel composition and to a novel preparation of said phosphites. More specifically this invention relates to the mono-alkyl mono-phosphite and di(mono-alkyl)phosphite of a tetramer comprising two moles of a dialkylphenol and two moles of a monoalkyl phenol and the preparation thereof by reacting the tetramer with a trialkyl phosphite at a temperature above 50° C. in the presence of iodine as a catalyst.

BACKGROUND OF THE INVENTION

In the development of a petroleum lubricating oils the trend has been directed to more and more drastic refining methods to reduce the tendency of such oils to form carbon and/or sludge deposits. While such highly refined oils possess many advantages, their resistance to oxidation, particularly under severe operation conditions, is generally decreased; they are more prone to form acidic oxidation products which are corrosive, and which cause undesirable increases in the viscosity of the lubricant.

To overcome the tendency of such highly refined oils to form carbon and/or sludge deposits on various operating parts of the engine, such as pistons, rings, valves, etc., various oil-soluble metal-containing detergent compounds now well-known in the art, have been incorporated in lubricating oil compositions. Such metal-containing organic compounds, while effective as detergents for dispersing the precursors of deposits within the oil itself, rather than permitting them to form deposits on the engine parts, had the disadvantage of forming ash deposits in the engine. To overcome this disadvantage, so-called ashless detergents were developed, and are now well-known in the art.

The organic compounds, both the metal-containing and the ashless, while imparting detergency properties to the lubricating oil compositions containing the same do not inhibit the oxidation of such lubricating oil compositions at high temperature operating conditions.

It has been reported by K. J. Humpris and Gerald Scott (JCS Perkins II, pp. 826–830, 1973) that catechol phosphites unexpectedly react quite rapidly with cumene hydroperoxides. Such rapid reaction was attributed by the authors to the in situ formation of ion-radicals by the phosphites which catalyze the decomposition of the hydroperoxides. Further, the authors reported that cyclic phosphites as enhancers of hydroperoxide decomposition are more effective than simple esters of phosphorous acid.

We, therefore, set out to find an oil-soluble polyhydroxy compound which could be converted to a cyclic phosphite by a commercially feasible preparation. Our tetramers of a mixed alkyl phenol described in our U.S. Pat. No. 3,876,709 are soluble in lubricating oils and have spacially close pairs of hydroxy groups (benzene ring carbons are joined to a benzene ring carbon connecting ortho positions to form the tetramer) which might, if reaction conditions were found, lend themselves to formation of a cyclic phosphite. Such tetrameric alkylphenols are obtained from ring carbon joining of a 2,4-dialkylphenol and a p-alkylphenol and can be represented by the following formula:

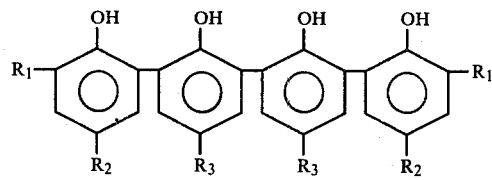

wherein $R_1$, $R_2$, and $R_3$ can be the same or can be different alkyl hydrocarbon groups. Such tetramers are poly-hindered phenols because all positions ortho to the hydroxyls are substituted by either alkyl or aromatic moieties. Preferably $R_1$ and $R_2$ are the same size alkyl hydrocarbon groups of from one to twelve carbon atoms and $R_3$ is a different alkyl hydrocarbon group whose carbon atom content makes the sum of carbons in the six R groups equal to from 44 to 72 or greater.

SUMMARY OF THE INVENTION

The oil-soluble poly-hindered alkyl phenol mono-alkyl and di(mono-alkyl) phosphites of this invention contain in their structure at least one and up to two cyclic phosphite groups of the following structures:

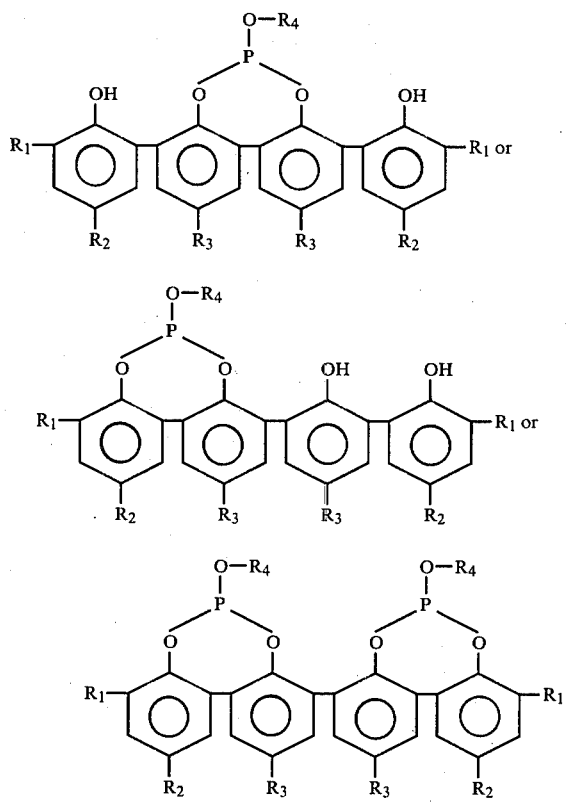

wherein $R_1$, $R_2$ and $R_3$ are as in the above tetramer and wherein $R_4$ is an alkyl hydrocarbon group of from one to four carbon atoms coming from the phosphorus containing reactant used to form the cyclic phosphite structure. The present inventive compositions will have one of such cyclic phosphite structures when the hydrogens of the central two hydroxyl groups are removed by the reaction forming such cyclic structure. But the present inventive compositions can have two such cyclic phosphite structures when hydrogens of each central and each lateral hydroxyl groups are removed by the reaction forming the cyclic phosphite structure.

As previously stated the foregoing hindered alkyphenol mono-alkyl and di(mono-alkyl) phosphites are prepared by reaction between the poly-hindered alkyl phenol tetramer and a trialkyl phosphite in the presence of catalytic amounts of iodine at temperatures above 50° C. Under relatively mild conditions the use of the reactants in the proportions of one gram mole of the tetramer and two gram moles of the trialkyl phosphite results in only one of the foregoing cyclic mono-alkyl diaryl cyclic phosphite structures. It is not known with certainty whether such mono-cyclic structure results from replacement of hydrogens on two central hydroxyl groups or from replacement of hydrogens from one central hydroxyl group and one lateral hydroxyl group. Under more severe reaction conditions and using reactants in the proportions of four or more gram moles of trialkyl phosphite to one gram mole of tetramer the present inventive compositions containing two mono-alkyl substituted cyclic phosphite structures might be obtained.

The cyclic phosphite structure forming reaction can be conducted, and is preferably conducted, in the presence of a reaction diluent. The reaction diluent can be an inert hydrocarbon boiling at a temperature of from 35° C. up 175° C. which includes; for example, the $C_5$ to $C_{10}$ alkanes; cyclohexane; and the, arenes benzene, toluene and the xylenes. The amount of reaction diluent used is not critical with respect to the inventive composition and is only a matter of convenience in making a low viscosity easily stirred reaction medium. The reaction diluent is removed from the reaction product as a means for isolating the inventive composition. As or after the reaction diluent is removed it can be replaced with a light grade lubricant oil such as SAE 5 or SAE 10W lubricant oil to keep in solution in less viscous form the rather viscous cyclic phosphite structure containing inventive composition; especially those having $R_3$ groups containing more than 12 carbon atoms.

The tetrameric poly-hindered phenol reactant can be prepared in any well known manner for achieving the ring carbon-to-ring carbon coupling. Conveniently such coupling of phenol units can be accomplished by oxidative coupling and preferably by the technique disclosed in our before-mentioned U.S. Pat. No. 3,876,709. Such preferred oxidative coupling can be accomplished in glacial acetic acid with an alkali metal (sodium, potassium or lithium) dichromate as the oxidant in the presence of a manganese salt (acetate, naphthenate, propionate, cumate, benzoate, etc.) as catalyst and water as reaction promoter. The mixture of alkylphenols, reaction solvent, oxidant, and catalyst is stirred until homogeneous and then water is added slowly. Upon additions of water the temperature of the reaction mixture increases. Thus heat removal is necessary to maintain the reaction at a temperature below 100° C., preferably below 95° C. Generally the evolution of heat ceases in 2 to 4 hours. However, the reaction mixture can be, without adverse effect, stirred for a longer period, say up to 12 hours, beyond reaction initiation.

Thereafter the reaction mixture is filtered to remove all salts. The resulting acetic acid solution is diluted with hexane and then washed with water to remove the acetic acid. Finally the hexane is removed by distillation while injecting nitrogen gas to assist in removing hexane and water to a final temperature of 145° C. to 150° C.

Preparation I

More specifically such preparative method is conducted, for example, with one gram mole portions of each of p-dodecylphenol (262 grams) and of 2,4-dinonyl phenol (336 grams) dissolved in one liter of glacial acetic acid to which are added 0.5 gram mole (147 grams) sodium dichromate and 10 grams manganous acetate tetrahydrate as catalyst. The resulting mixture is stirred until homogeneous at 20° C. Thereafter 100 ml of water is added slowly to the stirred mixture. An increase in reaction temperature of 25.6° C. is observed and heat of reaction is removed by cooling to maintain the oxidation reaction below 93° C. All the water is added in a 30 minute period. After about three hours from the time the water has been added no further heat of reaction is noted. Cooling is stopped and the reaction mixture's temperature does not increase.

The entire reaction mixture is filtered to separate insoluble salts from the acetic acid solution. The recovered filtrate solution is diluted with one liter of hexane and is washed until the wash water is no longer acidic indicating completion of removal of acetic acid. The hexane solution containing some wash water is heated to distill off the hexane. At about the completion of removal of 50% of the hexane, nitrogen gas is injected into the heated liquid until the liquid reaches a temperature of 149°–150° C. The remaining liquid is quite viscous. The molecular weight of said liquid is determined and found to have an average molecular weight of 1232. The theoretical molecular weight of two molecules of dinonylphenol and two molecules of dodecylphenol is 1210. Infrared identification shows free hydroxyl at 2530 $cm^{-1}$. The large reduction in adjacent hydrogen atoms together with the favorable comparison of average and theoretical molecular weights favors the correctness of the tetramer structure before given wherein all $R_1$ and $R_2$ groups are nonyl groups and all $R_3$ groups are dodecyl groups.

Preparation II

In a like manner a tetramer product from one gram mole portions of each of p-($C_{42}$ alkyl) phenol, whose alkyl group is derived from a polypropene used to alkylate phenol, and 2,4-dimethylphenol. Such tetramer is ultimately dissolved in benzene rather than hexane so that acetic acid can be washed out. The benzene solution is dried and retained. Such tetramer has all $R_1$ and $R_2$ groups as methyl groups and all $R_3$ groups as said $C_{42}$ alkyl groups.

Preparation III

Also in a like manner but using xylene as the ultimate solvent in place of hexane there is prepared a tetramer from equimolecular proportions of 2,4-tertiary butylphenol and p-($C_{200}$ alkyl) phenol whose alkyl group is derived from an isobutylene polymer to alkylate phenol. The acetic acid-and water-free xylene solution contains the tetramer whose $R_1$ and $R_2$ alkyl groups are all tertiary butyl groups and whose $R_3$ groups are said $C_{200}$ polybutyl groups.

Preparation IV

Equimolecular proportions of 2,4-di($C_8$ alkyl) phenol and p-($C_8$ alkyl) phenol, whose alkyl groups are derived from isobutylene dimer, are used in the above reaction. The ultimate solvent is octane instead of hexane. After washing acetic acid from the octane solution it is dried by heating it to 100° C. and injecting dry nitrogen gas into the solution. The octane solution is retained. Said solution contains the tetramer of the before presented formula wherein all of the $R_1$, $R_2$, and $R_3$ groups are isobutylene dimer groups.

SPECIFIC EMBODIMENTS OF THE INVENTION

The following four examples illustrate specific embodiments of the present invention wherein each of the poly-hindered phenol phosphite products contain one cyclic phosphite of the structure before given.

EXAMPLE 1

A one hundred gram (0.081 gram mole) sample of Preparation I, the tetramer having four (all $R_1$ and $R_2$ groups) nonyl groups and two (both $R_3$ groups) dodecyl groups, is taken and dissolved in benzene. To the benzene solution there is added 200 ml (0.162 gram mole) of triethyl phosphite (a molar excess) and one gram of iodine as catalyst. The mixture is stirred and heated to a temperature of 93°–94° C. The stirred reaction mixture is held at that temperature for about 120 minutes. Thereafter benzene, by-product ethanol and excess triethyl phosphite are removed by distillation under subatmospheric pressure. By analysis the product is found to have an average molecular weight of 1302 (theoretical molecular weight of 1306) and a phosphorous content of 2.6 weight percent (theoretical phosphorous content is 2.45 weight percent).

EXAMPLE 2

A sample of the benzene solution of Preparation II is taken containing 0.20 mole of the tetramer having four methyl groups and two $C_{42}$ polypropyl groups. To this solution are added 0.4 gram mole (a molar excess) of trimethylphosphite and two grams of iodine as catalyst. The reaction mixture is stirred and heated to 95° C. and held at that temperature for three hours. Thereafter the solvent, methanol and ecess trimethyl phosphite are removed by distillation under sub-atmospheric pressure. The resulting process upon analysis will be found to have an average molecular weight and phosphorous content as close to the theoretical as was the case in Example 1.

EXAMPLE 3

A sample of the xylene solution of Preparation III is taken containing 0.15 gram mole of the tetramer containing four tertiary butyl groups and two $C_{200}$ polybutyl alkyl groups. The solution is stirred and to the stirred solution there are added 0.30 gram mole of triethylphosphite and 1.2 grams of iodine as catalyst. The stirred mixture is heated to 100° C. and held at that temperature for two hours. Xylene, ethanol and excess triethyl phosphite are removed under reduced pressure. The residual product contains one cyclic phosphite structure as before shown as indicated by its average molecular weight and phosphorous content which are quite near the theoretical values.

EXAMPLE 4

A sample of octane solution of preparation IV is taken containing 0.1 gram mole (87.4 grams) of the tetramer whose all six alkyl groups are isobutene dimer ($C_8$) alkyl groups. The solution is stirred and there are added thereto 0.25 gram mole of triethyl phosphite and 2 grams of iodine as catalyst. The stirred mixture is heated to 92° C. for 2.25 hours. Thereafter octane, ethanol and excess triethyl phosphite are removed by distillation at subatmospheric pressure. The residual material, having an average molecular weight and phosphorous content close to the theoretical values is an illustrative product of the present invention.

The products of the present invention are effective oxidation inhibitors in oleaginous lubricant compositions when used in amounts of from about 0.1% to about 10%. Suitable lubricating base oils are mineral hydrocarbon oils, i.e., petroleum oils, synthetic lubricating oils, such as those obtained by the polymerization of hydrocarbons, and other well-known synthetic lubricating oils such as the sebacate esters and adipate esters. Concentrates of suitable oil bases containing more than 10%, i.e., from about 10% to about 75% or more, of the additive of the present invention can be used for blending with base lubricating oils in proportions desired for particular conditions of use. Lubricating oil compositions containing the additives of the present invention can contain other well-known additives to impart other desired properties to the lubricant composition.

To illustrate the oxidation inhibition ability of the product of this invention, the following standard lubricant oil thickening test is conducted. A SAE 10W-30 formulated oil (grams) is heated to 171° C. and held at that temperature while air at the rate of 60 cubic centimeters per minute are injected into the hot oil until the viscosity of the oil increases at least fourfold. The number of hours for the viscosity to quadruple (4Vo) is reported. Also at the end of 48 hours a sample of the oil is taken and measured for its sludge dispersancy. Such sludge dispersancy is measured by placing replicate drops of oil on a sheet of blotting paper. The base oil forms a ring. If the initial dispersant is still functioning the sludge ring will be as large as the base oil ring otherwise the sludge ring is smaller than the base oil ring. The results of this test are reported as the ratio of sludge ring to oil ring X 100 and represents percent dispersancy retained.

Two oil formulations were tested as above described. Each formulation contained the same base oils, the same Viscosity Index improver, the same dispersant and the same rust inhibitor, all commercially used and accepted addition agents. The only difference between the two formulations A and B is that Formulation A contains the product of illustrative Example 1 and Formulation B contains one of the leading oxidation inhibitors for lubricant oils. The results of the oil thickening (quadrupled viscosity) tests and the sport dispersance tests for Formulations A and B are reported in Table I to follow:

TABLE I

| | Hours to 4Vo | % Retained Dispersancy after 48 hours |
|---|---|---|
| Formulation A with 1.9 wt % product of Example 1 | 120 | 100% |
| Formulation B with 1.9 wt % of Commercial anti-oxidant | 46 | 86% |

An oil formulation containing the product of Example 1 is tested in the Falex (wear) test and a bearing corrosion test. To pass the Falex test the oil must go to lubricant failure of at least 1700 pounds. To pass the bearing corrosion test the bearing must not have lost more than 30 milligrams of lead and not more than 5 milligrams of copper. An oil formulated to contain 7.0% dispersant, 0.7% rust inhibitor, 2.9% varnish control additive 1.0% wear inhibitor, and 1.9% of the product of Example 1 (all % are by weight). The bearing weight loss test is conducted 20 hours with the oil at 150° C., with air injected into the oil at 60 cc per minute and in the presence of ferric naphthenate as corrosion catalyst. The formulation containing the product of Example 1 caused a lead loss of 1.2 milligrams and no copper loss. In the Falex (wear) test said formulation did not fail at 1700 pounds pressure but rather went to 2140 pounds pressure on the lubricated surfaces before it failed.

The invention claimed is:

1. A mono-cyclic phosphite and dicyclic phosphite derived from a hexa-alkyl substituted phenol tetramer which have the structural formulae:

Monocyclic I:

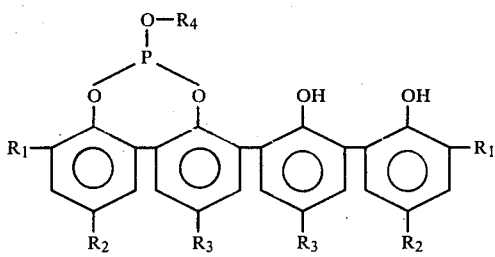

Monocyclic II:

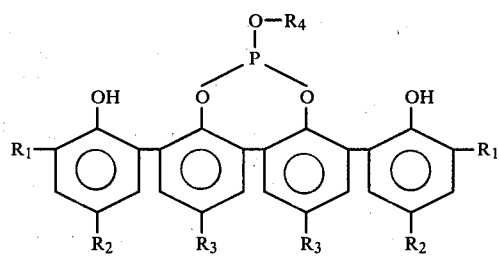

Dicyclic:

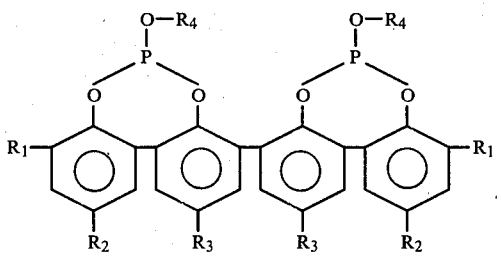

wherein $R_4$ is an alkyl hydrocarbon group containing one to four carbon atoms, the groups $R_1$, $R_2$, and $R_3$ are also alkyl hydrocarbon groups of a size such that the total carbon atom content for the six such groups is at least 42 carbon atoms.

2. The cyclic phosphite structure-containing compound of claim 1 wherein the $R_3$ groups each contain from eight to 200 carbon atoms.

3. The cyclic phosphite structure-containing compounds of claim 2 wherein the group $R_1$ and $R_2$ each contain from 1 to 12 carbon atoms.

4. The cyclic phosphite structure-containing compounds of claim 3 wherein each $R_1$ and $R_2$ is the nonyl groups and each $R_3$ group is the dodecyl group.

5. The cyclic phosphite structure-containing compound of claim 3 wherein each of the $R_1$ and $R_2$ is methyl groups and each of the $R_3$ groups is $C_{42}$ alkyl groups derived from a polypropene.

6. The cyclic phosphite structure-containing compound of claim 3 wherein each of the $R_1$ and $R_2$ groups is the tertiary butyl group and each of the $R_3$ groups is the $C_{200}$ alkyl group derived from a polybutene.

7. The cyclic phosphite structure-containing compound of claim 3 wherein each of the $R_1$, $R_2$, and each $R_3$ group is the isobutene dimer group.

8. The method of preparing a cyclic phosphite structure-containing compound of claim 1 which comprises reacting in the presence of a catalytic amount of iodine a poly-hindered phenol tetramer of the formula:

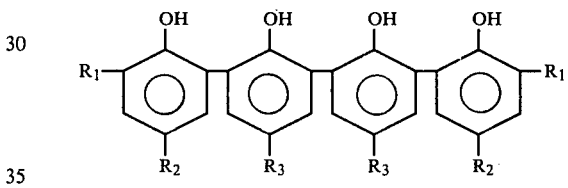

wherein the groups $R_1$, $R_2$, and $R_3$ are alkyl hydrocarbon groups whose total carbon content is at least 42; with a tri($C_1$ to $C_4$ alkyl) phosphite used in at least a molar excess over the equimolar proportions for the mono-cyclic phosphite structural compounds and over the 1 to 2 molar proportions for the dicyclic phosphite structured compound reacted in the presence of an inert hydrocarbon diluent boiling between the temperatures of 35° C. and 175° C. and at the reaction temperature of above 50° C. but not exceeding 100° C. followed by removing at least the coproduct $C_1$ to $C_4$ alkanol and excess trialkyl phosphite.

9. The method of claim 1 wherein the trialkyl phosphite is triethyl phosphite.

10. The method of claim 1 wherein the trialkyl phosphite is trimethyl phosphite.

11. The method of claim 1 wherein the tetramer has for its $R_1$ and $R_2$ groups the nonyl groups and for its $R_3$ groups the dodecyl groups the molar ratio of triethyl phosphite to tetramer is 2:1 and the reaction solvent is benzene.

* * * * *